United States Patent [19]

Szalóki et al.

[11] Patent Number: 5,468,492
[45] Date of Patent: Nov. 21, 1995

[54] COSMETIC COMPOSITION

[75] Inventors: Erzsébet Szalóki; Ilona Kristóf; Veronika Pál; Eva Szabó, all of Debrecen, Hungary

[73] Assignee: Biogal Gyógyszergyár RT, Debrecen, Hungary

[21] Appl. No.: 174,202

[22] Filed: Dec. 27, 1993

[30] Foreign Application Priority Data

Jul. 27, 1993 [HU] Hungary ............... P 93 02175

[51] Int. Cl.⁶ .................................................. A61K 35/78
[52] U.S. Cl. .................. 424/195.1; 424/70.1; 424/74
[58] Field of Search ................... 424/195.1, 74, 424/70

[56] References Cited

U.S. PATENT DOCUMENTS

| | | | |
|---|---|---|---|
| 4,702,915 | 10/1987 | Réri et al. | 424/195.1 |
| 5,043,323 | 8/1991 | Bombardelli et al. | 514/25 |
| 5,080,901 | 1/1992 | Hangay et al. | 424/195.1 |

OTHER PUBLICATIONS

Fenwick et al. *Food Chemistry*, vol. 38(2), pp. 119–143, (1990), (Abstract Only).
Rovesti et al.; Chemical Abstracts 81:126679u (1974).
Ikeda et al.; Chemical Abstracts 103:98433m (1985).
Azimov et al.; Chemical Abstracts 109:104381k (1988).
Tsutsumi; Chemical Abstracts 113;84638b (1990).
Steinmetz, Codex Vegetabilis, 1957 No. 525 p. 517/525 and 526/534.

*Primary Examiner*—Douglas W. Robinson
*Assistant Examiner*—Howard C. Lee
*Attorney, Agent, or Firm*—Schweitzer Cornman & Gross

[57] ABSTRACT

A topical cosmetic composition of an extract of a hair fallout reducing effective amount of *Gingko biloba* (maidenhair tree) leaves, and an extract of the root of *Liquiritia officinalis* (sweet-root), and one or more cosmetically acceptable solid or liquid carrier, and optionally one or more cosmetically acceptable supplementary ingredient.

12 Claims, No Drawings

COSMETIC COMPOSITION

FIELD OF THE INVENTION

The present invention relates to a cosmetic composition, more particularly to a cosmetic composition for improving the functioning of hair roots, being particularly effective for ameliorating or eliminating the falling out of hair.

BACKGROUND OF THE INVENTION

The falling out of hair is a problem for many people everywhere. This can occur for various reasons such as aging, biochemical changes of the organism, endocrine disturbance, and environmental harms.

A number of compositions are known from the literature and various drugs are commercially available which can ameliorate the falling out of hair. Some of them can be taken orally, others are topical compositions, but it is a common feature of such agents that they do not function in the same manner or equally well. In some cases the compositions slow down the falling out of hair. In other cases they are entirely ineffective. Therefore, new compositions are constantly marketed for such purposes.

Some compositions for preventing the falling out of hair contain capsaicin, nettle extract, or horseradish extract for causing local hyperaemia. A preparation described in Hungarian patent No. 155,510 contains chamomile extract and *Oleum carbi*. The compositions of French patents Nos. 1,443,889 and 1,481,008 contain various plant extracts. A hair tonic is described in Hungarian patent No. 166,460, containing *Populus canadiensis* and *Populus nigra piramidalis*. According to Hungarian patent No. 169,439 the horseradish extract can be used as active ingredient for the aforementioned purpose.

DESCRIPTION OF THE INVENTION

It is an object of the present invention to provide a composition containing natural active ingredients which improve the root functions of hair and decrease the falling out of hair. It is another object of the invention to provide a composition for nourishing the scalp and increasing its blood supply.

During our experimentation we have found that these objects can be achieved surprisingly by a composition containing an extract of a plant component, namely from about 5% to about 40% wt. of an extract of the leaves of *Gingko biloba* (maidenhair tree), or from about 3% to about 35% wt. rootstock and/or root extract of *Liquidtia officinalis* (sweet-root), or of a mixture of these extracts, together with a cosmetically acceptable carrier, to make it 100%. As used throughout the specification and the claims, the term "carrier" is used interchangeably with, or in addition to "diluent", "excipient" and the like expression for a cosmetically acceptable additive. Further, as used throughout the specification and the claims, reference to "root" is also intended to refer to "rootstock" alone, or both to "root" and to "rootstock". Similarly, any reference to an extract of root, is also intended to encompass any extract of rootstock alone, or a mixture of root and rootstock or extracts of root and rootstock.

It is known that the extract of *Gingko biloba* (maidenhair tree) leaves administered orally is used for the treatment of oedema, senile vertiginous complaints, and defective memory. According to analytical examinations the leaf contains flavonoid derivatives, mono- and diglycosides thereof formed with glucose and rhamnose, luteolin derivatives such as delphidenon, and delphidenon glycoside, biflavones such as ginkgetin, isoginkgetin, and bilobetin, as well as proanthocyanidines, catechins; cyclic terpene derivatives, sitosterol, sitosterol glycosides, fatty oils, sugars and organic acids.

DETAILED DESCRIPTION OF THE INVENTION

The extract of roots and rootstock of *Liquiritia officinalis* (sweet-root) has bacteriostatic effect, and is conventionally applied orally in the therapy of upper respiratory diseases. The drug contains triterpene, saponin, including glycyrrhizin and derivatives thereof, glabranin A and B, isoglabrolide, flavonoids, coumarins such as umbelliferone, and herniarin, sugars, starch, bitter materials, amino acids, sterols and volatile oils.

The composition of the present invention contains the extracts of the above mentioned plant components obtained by extraction with water and/or alcohol, and/or with water immiscible organic solvents, suitably an oil.

The extract can be prepared by conventional methods, for example by extracting the optionally dried plant components with from about 2 to about 30 times as much liquid as the amount of the dried plant component, suitably at from about 15° C. to about 95° C., and then separating the plant components from the liquid phase.

The extraction can be carried out by using parallel-current or counter-current flow techniques, steeping, or boiling. Suitably the phases are contacted intensively with each other and at elevated temperature to shorten the extraction time. The germ content can be reduced, for example, by tyndallization. Water, ethanol, or a cosmetically acceptable water immiscible organic solvent, suitably mineral oil can be used as the extrahand.

The cosmetic composition of the invention can contain one or more cosmetically acceptable liquid solvents or diluents e.g. water, ethanol, vegetable or animal oils, which do not irritate the skin.

The cosmetic composition of the present invention can also contain one or more carriers and/or excipients and/or supplementary materials. A solid carrier can be one or more of talc, zinc oxide, bentonite, kaolin, colloidal silica, titanium dioxide, cornstarch, and potato starch. Solid emulsifiers such as fats, fatty alcohols, fatty acid esters or waxes can also serve as a solid carrier.

A carrier or emulsifier can also be a fat, oil, wax, fatty acid, and an ester thereof formed with a long chain alcohol or glycerol usually of the type conventionally used in the cosmetic industry. Suitably $C_{12-18}$ straight or branded chain saturated or unsaturated fatty acids are used in the cosmetic composition of the present invention and can be substituted by one or more hydroxy groups. Suitable fatty acids include undecylenic acid, lauric acid, caprylic acid, myristic acid, palmitic acid, isopalmitic acid, stearic acid, isostearic acid, hydroxy stearic acid, oleic acid, hydroxy oleic acid, behenic acid, lanolin fatty acid, arachidic acid, octyl decanoic acid, pentadecanoic acid, and mixtures thereof.

Fatty esters can be used to improve the tactile properties of the composition. Suitable fatty acid esters include isopropyl myristate, butyl myristate, cetyl myristate, ethyl palmirate, isopropyl palmitate, hexadecyl stearate, isopropyl isostearate, isostearyl isostearate, diisopropyl sebacate, cetyl ricinolate, propylene glycol dipelargonate, 2-ethyl-hexyl isononate, 2-ethyl-hexyl stearate, one or more $C_{12-16}$ fatty alcohol lactates, triglycerides of octanoic acid, and decanoic acid, isopropyl lanolate, 2-ethyl-hexyl salicylate and mixtures thereof. The most suitable fatty acid esters are isopropyl myristate, butyl stearate, hexyl laurate, octyl-dodecyl myristate, diisopropyl adipate, diisopropyl sebacate, and isocetyl myristate.

Suitable fatty alcohols include $C_{14-22}$ alkanols such as stearyl, myristyl, behenyl, arachidyl, isostearyl, cetyl, isocetyl, oleyl, lauryl alcohols.

The compositions of the present invention can also contain as liquid carrier an oil conventionally used in the cosmetic industry and mixtures of such oils. These increase the stability of the emulsion and can provide a cosmetically suitable viscosity.

The oils which can be suitably used include aliphatic hydrocarbons (such as liquid paraffin, petrolatum, ceresin and the like), vegetable fats and oils (such as olive oil, jojoba oil, avocado oil, castor oil, cocoa butter, palm oil), animal fats and oils (such as cod-liver oil, whale oil, and butterfat).

The compositions of the present invention can further contain one or more supplementary ingredients such as one or more vitamins, blood circulation improving agents, disinfectants, epithelium regenerating materials, skin soothers, preservatives, thickeners, anti-fading agents, stabilizers, antioxidants, moisture absorbents, fragrances, filmforming materials, and refatting agents.

Methylparaben, other esters of p-hydroxy-benzoic acid, chloro-methyl-thiazoline, methyl-isothiazoline, phenyoxyethol, hexetidine, chloro-hexydingluconate, imidazolidinylurea and the like can be used as preservatives.

Suitably volatile oils can be used as a flagrance to provide a pleasant and attractive scent.

Suitable anti-fading agents include octyl-diemthyl-PABA, 2-hydroxy-4-methoxybenzophenone, 2-( ethyl-hexyl )-3-( 4-methoxy-phenyl)-2-propenoate, 1-4(methoxy-phenyl)-3-(4 -tert-butyl-phenyl)-propane-1,3-dione, urocanic acid, and esculin.

Suitable stabilizers include butyl-hydroxy-anisole, butyl-hydroxy-toluene, ethylene-diamine-tetraacetic acid, and nordihydroguaiaretic acid.

Refatting agents that can suitably be used according to the present invention include 1-(alkylamino)-3-(dimethylamino)-propane-3-N-oxide, propane-3-(dimethylamino)-propane-3-N-oxide, propane-3-( carboxy-methyl)-betaine, alkyl-dimethylaminooxide, and mono-or diethanol-amide of coconut acid.

Filmforming materials suitably include the copolymers of vinyl-imidazoliummethylchloride and vinyl-pyrrolidone, cetyl-dimethyl-2-(2-hydroxy-ethyl)-ammonium-dihydrogen-phosphate.

One or more of vitamins A, B, C, E, F, H, and P can be advantageously employed.

Capsaicin, Vitamin E nicotinate, nicotinic acid benzyl ester, rosemary extract, chestnut extract and the like can be applied for improving the circulation of blood of the scalp.

Glycerol, sorbitol, and propylene-glycol can be used as a moisture absorbent.

Cellulose and derivatives thereof, alginic acid and derivatives thereof, acrylic acid copolymers and its sodium salt and polyoxyethylene-(150)-distearate can be used as thickeners.

One or more of allantoin, panthenol, and calcium panthotenate can be used for regenerating the epithelium.

Chamomile extract, azulenole, bisabolol and the like can be used as skin soothers.

Menthol, camphor, lactic acid, citric acid, and ethanol can be used as disinfectants.

The quantity of water or aqueous carrier depends on the desired consistency of the end product. Suitably from about 30% to about 90% wt. deionized, demineralized, or distilled water is used, most suitably from about 40% to about 85% wt based on the total composition. Suitably, the composition of the present invention contains at least about 25% wt. but less than about 50% wt. water when the composition is in the form of a cream or ointment and at least 75% wt. when the composition is in the form of a tonic of other liquid form cosmetics. Any cosmetically acceptable cation containing alkaline neutralizing agent, for example potassium hydroxide, sodium hydroxide, mono-, di-, and triethanolamine can be used for adjusting the pH of a liquid composition of the present invention, such as in the form of a solution or tonic, to from about pH 6.5 to about 7.5. When an alkaline neutralizing agent, such as an ethanolamine, is employed it can at the same time be also employed as an emulsifier.

The preparation of the active ingredient plant extracts of the cosmetic composition of the present invention are illustrated in the following further illustrative examples.

EXAMPLE 1

1 kg of dry maidenhair tree (*Gingko biloba*) leaves is washed thoroughly with deionized water, then placed into an extractor and 10 liters of deionized water is circulated at 85° C. through the extractor for 60 minutes.

The extract is cooled to 30° C., filtered, then pressed into a previously sterilized stainless steel tank by water steam and is heated three times to 80° C. for 60 minutes, with 24 hours intervals between the heatings. Thereafter, the mixture is cooled and kept in a dry, cold place until further use.

EXAMPLE 2

1 kg of dry of maidenhair tree (*Gingko biloba*) leaves is washed thoroughly with demineralized water, then placed into an extractor and 10 liters of 70v/v% aqueous ethanol is circulated through the extractor at 50° C. for 60 minutes. The extract is cooled to 25° C. and filtered.

EXAMPLE 3

1 kg of dry of maidenhair tree (*Gingko biloba*) leaves is ground and steeped in 3kg of cosmetic grade mineral oil for 24 hours. The mixture is stirred once each hour and then the oil extract is filtered.

EXAMPLE 4

1 kg of dry maidenhair tree (*Gingko biloba*) leaves is washed thoroughly with demineralized water, then it is ground together with 2.5 kg of demineralized water, steeped for 18 hours and filtered. The extract is heated at 80° C. as in Example 1, then cooled and is stored in a dry cold place.

EXAMPLE 5

1 kg of dry sweet-root (*Liquiritia officinalis*) is washed thoroughly with demineralized water, then placed into an extractor and 10 liters of demineralized water of is circulated at 95° C. through the extractor for 50 minutes. Then the mixture is cooled to 30° C., filtered and treated at 80° C. as in Example 1.

EXAMPLE 6

1 kg of dry sweet-root (*Liquiritia officinalis*) is ground with 8 liters of demineralized water, steeped for 16 hours and then filtered. The plant extract is heat treated at 80° C. as in Example 1.

Example 7

1 kg of dry sweet-root (*Liquiritia officinalis*) is washed thoroughly with demineralized water, then placed into an extractor and 5 liters of 70v/v% aqueous ethanol is circulated at 50° C. through the extractor for 60 minutes. The extract is cooled to 25° C. and filtered.

EXAMPLE 8

1 kg of dry sweet-root (*Liquiritia officinalis*) is ground, steeped in 5 kg of mineral oil for 24 hours, the mixture is stirred once each hour and then filtered.

EXAMPLE 9

0.5 kg dry sweet-root and 0.5 kg dry leaves of the maidenhair tree is washed with demineralized water, ground and then steeped in 30 kg propylene glycol at 15° C. for 6 days, with occasional stirring. The plant solids are pressed and then the liquid phase is filtered off.

EXAMPLE 10

0.5 kg dry sweet-root and 0.5 kg dry leaves of maidenhair tree is washed with demineralized water, and then steeped in 15 kg of ethanol of 96 v/v% at 20° C. The plant solids are separated from the liquid phase by filtration.

EXAMPLE 11

0.5 kg dry sweet-root and 0.5 dry leaves of the maidenhair tree is washed with demineralized water, then steeped in 12 kg of mandelic oil at room temperature for 3 days with occasional stirring. The plant solids and the liquid phase are separated by filtration.

| | % wt |
|---|---|
| Example 12, Nourishing cream for dry hair | |
| Oil extract of Example 3 | 10 |
| Oil extract of Example 8 | 7 |
| Mandelic oil extract of Example 1 | 13 |
| Cetyl alcohol | 2 |
| Stearin | 5 |
| Castor oil | 4 |
| Cremophor A 6 (BASF) (ethoxylated fatty alcohol and stearyl alcohol) | 3 |
| Cremophor A 25 (BASF) (ethoxylated fatty alcohol) | 3 |
| Lanette N (Henkel) (sodium cetyl stearyl sulfate and cetyl stearyl alcohol) | 2 |
| Methyl p-hydroxy-benzoate | 0.2 |
| Vitamin E nicotinate | 0.5 |
| Fragrance | 0.2 |
| Demineralized water q.v. 100% | |
| Example 13, Nourishing cream for normal hair | |
| Aqueous extract of Example 1 | 15 |
| Aqueous extract of Example 6 | 10 |
| Walnut oil | 5 |
| Sodium lauryl sulfate | 0.6 |
| Vitamin H | 0.25 |
| Rosemary oil | 1 |
| Panthenole | 2 |
| Methyl p-hydroxy-benzoate | 0.2 |
| Vitamin E | 0.03 |
| Glycerol monostearate | 2 |
| White petrolatum | 2 |
| Stearin | 3 |
| Cetyl alcohol | 2 |
| Fragrance | 0.2 |
| Deionized water q.v. 100% | |
| Example 14, Nourishing cream for fatty hair | |
| Alcoholic extract of Example 2 | 18 |
| Alcoholic extract of Example 7 | 5 |
| 1-hydroxy-4-methyl-6-(2,4,4-trimethyl-penthyl)-2(1H)-pyridone ethanolamine salt | 1 |
| Panthenol | 3 |
| Vitamin H | 3 |
| Cetyl stearyl-2-ethyl-hexanoate | 2 |
| Imidazolidinyl-urea | 0.2 |
| Corn oil | 2 |
| Vitamin E nicotinate | 0.7 |
| Fragrance | 0.2 |
| Demineralized water q.v. 100% | |
| Example 15, Nourishing gel for dry hair | |
| Aqueous extract of Example 4 | 20 |
| Oil extract of Example 8 | 5 |
| Hazelnut oil | 4 |
| Methylcellulose | 0.5 |
| Polyoxy-ethylene (20)-sorbitan-monolaurate | 5 |
| Rosemary oil | 1 |
| Vitamin H | 0.5 |
| Panthenol | 5 |
| 1-hydroxy-4-methyl-6-(2,4,4-trimethyl-penthyl)-2(1H)-pyridone ethanolamine salt | 0.5 |
| Glycerol | 4 |
| Methyl p-hydroxy-benzoate | 0.2 |
| Octyl-dodecanol | 10 |
| Fragrance | 0.2 |
| Demineralized water q.v. 100% | |
| Example 16, Nourishing gel for normal hair | |
| Aqueous extract of Example 4 | 25 |
| Aqueous extract of Example 6 | 10 |
| Vitamin E nicotinate | 2 |
| Cetyl-stearyl-2-ethyl-hexanoate | 5 |
| Hydroxy-ethyl-cellulose | 1 |
| Polyoxy-ethylene-(20)-sorbitan-monolaurate | 7 |
| Sorbic acid | 0.1 |
| Panthenol | 3 |
| Fragrance | 0.2 |
| Demineralized water q.v. 100% | |
| Example 17, Nourishing gel for fatty hair | |
| Alcoholic extract of Example 10 | 20 |
| Hydroxy-ethyl-cellulose | 0.7 |
| Methyl p-hydroxy-benzoate | 0.1 |
| Benzyl nicotinate | 0.1 |
| Zinc-pyridinethione | 1 |
| Ethyl alcohol | 20 |
| Fragrance | 0.2 |
| Demineralized water q.v. 100% | |
| Example 18, Hair tonic for fatty hair | |
| Alcoholic extract of Example 2 | 23 |
| Alcoholic extract of Example 7 | 7 |
| Propylene glycol | 4 |
| Ethyl alcohol | 30 |
| Vitamin E nicotinate | 2 |
| Rosemary oil | 2 |
| Sorbic acid | 0.1 |
| Camphor | 0.1 |
| Demineralized water q.v. 100% | |
| Example 19, Hair tonic for dry hair | |
| Alcoholic extract of Example 1 | 30 |
| Alcoholic extract of Example 7 | 10 |

-continued

| | % wt |
|---|---|
| Propylene glycolic extract of Example 9 | 3 |
| Allantoin | 0.5 |
| Panthenol | 3 |
| Vitamin E nicotinate | 1 |
| Methanol | 10 |
| Methyl p-hydroxy-benzoate | 0.1 |
| Fragrance | 0.2 |
| Demineralized water q.v. 100% | |

Example 20, Hair dressing lotion

| | |
|---|---|
| Alcoholic extract of Example 1 | 15 |
| Alcoholic extract of Example 5 | 8 |
| Castor oil | 3 |
| Glycerol | 2 |
| Hydroxy-ethyl-cellulose | 1 |
| Zinc-pyridinethione | 2 |
| Capsicum extract | 3 |
| Methyl p-hydroxy-benzoate | 0.2 |
| Fragrance | 0.2 |
| Demineralized water q.v. 100% | |

The cosmetic composition of the present invention was applied as described in the following tests.

Test 1

The preparation of Example 16 was studied on a group of 30 individuals. The test subjects collected their falling hair each morning for two weeks. Then their remaining hair and scalp were treated with the composition of Example 16 by rubbing it into the hair and scalp after washing the remaining hair. The excess of the composition was removed after 20–30 minutes with lukewarm water, and the hair on the head was dried in the usual manner.

When after four-weeks of treatment once or twice each week, the subjects resumed collecting and counting their falling out hair each morning.

in 11 cases the falling out of the hair has stopped;

in 8 cases the falling out of the hair has significantly decreased (by about 40–50%);

in 7 cases the falling out of the hair has decreased (by about 10–20%); and in 4 cases no improvement was observed.

In about two thirds of the cases, dandruff formation decreased and the strength of the hair was improved.

Test 2

The treatment described in Test 1 was repeated on 30 test subjects with the composition of Example 16, except that it did not contain the *Gingko biloba* extract.

in 2 cases the falling out of the hair decreased by 40–50%;

in 3 cases the falling out of the hair decreased by 10–20%; and in 25 cases no improvement was observed.

Test 3

The treatment described in Test 1 was repeated with the composition of Example 16 but without the *Liquiritia officinalis* extract of Example 6.

in 4 cases the falling out of the hair decreased only by 10–20%; and in 26 cases no improvement was observed.

Test 4

The treatment described in Test 1 was repeated with the composition of Example 16, containing neither *Gingko biloba* extract nor *Liquidtia officinalis* extract.

in 2 cases the falling out of the hair decreased by 10–20%; and in 28 cases no improvement was observed.

We claim:

1. A topical cosmetic composition which comprises a hair fallout reducing effective amount of a mixture of an extract of *Gingko biloba* (maidenhair tree) leaves and an extract of the root of *Liquirita officinalis* (sweet root) combined with one or more cosmetically acceptable solid or liquid carrier, and optionally combined with one or more cosmetically acceptable supplementary ingredient.

2. The topical cosmetic composition of claim 1, wherein said effective amount of said *Gingko biloba* extract is from about 5% to about 40% wt based on the composition, and said effective amount of said *Liquiritia officinalis* extract is from about 3% to about 35% wt. on the same basis.

3. The topical cosmetic composition of claim 2, wherein any of said extract is of an oil or water extract, or a mixture of an extract with a cosmetically acceptable water miscible organic solvent and water.

4. The topical cosmetic composition of claim 2, containing one or more solid carrier selected from the group consisting of cetyl alcohol, glycerol monostearate and petrolatum.

5. The topical cosmetic composition of claim 2, containing one or more liquid carrier selected from the group consisting of hazelnut oil, castor oil, walnut oil, corn oil, ethanol, glycerol, octyl-dodecanol and cetyl stearyl hexanoate.

6. The topical cosmetic composition of claim 2, containing one or more supplementary ingredient selected from the group consisting of a vitamin, a rubefacient agent, a skin soothing agent and an epithelium conditioning agent.

7. The topical cosmetic composition of claim 1 further containing vitamin E.

8. The topical cosmetic composition of claim 2, further containing one or more rubefacient agent selected from the group consisting of rosemary extract, chestnut extract, vitamin E nicotinate and benzoyl nicotinate.

9. The topical cosmetic composition of claim 2, further comprising panthenol as an epithelium conditioning agent.

10. The topical cosmetic composition of claim 2, further containing allantoin as a skin soothing agent.

11. A cosmetic composition comprising:

(i)(a) from about 5% to about 40% by weight of an oil extract, water extract or an extract with a mixture of a water miscible organic solvent and water of Gingko biloba leaves and (b) from about 3% to about 35% by weight of a like extract of the root of *Liquirita officinalis;*

(ii) one or more carrier selected from the group consisting of an oil, a wax, a fatty acid, a fatty acid substituted by one or more hydroxy groups and a fatty acid ester formed with a long chain alcohol or with glycerol; and (iii) from about 30% to about 90% by weight water.

12. The topical cosmetic composition of claim 11, wherein (i) said fatty acid is one or more fatty acid selected from the group consisting of undecylenic acid, lauric acid, caprylic acid, myristic acid, palmitic acid, isopalmitic acid, stearic acid, isostearic acid, hydroxy stearic acid, oleic acid, hydroxy oleic acid, behenic acid, lanolin fatty acid, arachidic acid, octyl decanoic acid, pentadecanoic acid, and mixtures thereof;

(ii) said fatty acid ester is selected from the group consisting of isopropyl myristate, diisopropyl adipate, butyl myristate, butyl stearate, cetyl myristate, ethyl palmitate, isopropyl palmirate, hexyl laurate or sebacate, hexadecyl stearate, octyl-dodecyl myristate, isopropyl isostearate, isocetyl myristate, isostearyl isostearate, diisopropyl sebacate, cetyl ricinolate, propylene glycol dipelargonate, 2-ethyl-hexyl isononate, 2-ethyl-hexyl stearate, $C_{12-16}$ fatty alcohol lactate, a triglyceride of octanoic acid and of decanoic acid, isopropyl lanolate, and 2-ethylhexyl salicylate;

(iii) said oil and wax is one or more oil and wax selected from the group consisting of liquid paraffin, petrolalum, ceresin, olive oil, jojoba oil, avocado oil, castor oil, cocoa butter, palm oil, cod-liver oil, whale oil, and butterfat; said composition further comprising (iv) one or more optional preservative selected from the group consisting of methylparaben, an ester of p-hydroxy-benzoic acid, chloro-methyl-thiazoline, methylisothiazoline, phenyoxyethol, hexetidine, chloro-hexydingluconate, and imidazolidinyl-urea;

(v) one or more optional anti-fading agent selected from the group consisting of octyl-dimethyl-PABA, 2-hydroxy-4-methoxy -benzophenone, 2-(ethyl-hexyl)-3-(4-methoxy-phenyl)-2-propenoate, 1-4(methoxy-phenyl)-3-(4-tert-butyl-phenyl) -propane-1,3-dione, urocanic acid, and esculin;

(vi) one or more optional stabilizer selected from the group consisting of butyl-hydroxy-anisole, butyl-hydroxy-toluene, ethylene-diamine-tetraacetic acid, and nordihydroguaiaretic acid;

(vii) one or more refatting agent selected from the group consisting of 1-(alkylamino)-3-(dimethylamino)-propane-3-N -oxide, propane-3-(dimethyl-amino)-propane-3-N-oxide, propane-3-(carboxy-methyl)-betaine, alkyl-dimethylamino-oxide, and mono-or diethanolamide of coco fatty acid;

(viii) one or more optional film forming material selected from the group consisting of a copolymers of vinylimidazolium-methylchloride vinyl-pyrrolidone, and cetyl-diemethyl-2-(2-hydroxyethyl)-ammonium-dihydrogen-phosphate;

(ix) one or more optional vitamin selected from the group consisting of vitamin A, B, C, E, F, H or P;

(x) one or more optional rubefacient selected from the group consisting of capsaicin, Vitamin E nicotinate, nicotinic acid benzyl ester, rosemary extract, and chestnut extract;

(xi) one or more optional moisture absorbent selected from the group consisting of glycerol, sorbitol, and propylene-glycol;

(xii) one or more optional thickener selected from the group consisting of a cellulose, an alginic acid or alginate, an acrylic acid polymer, a salt of an acrylic acid, and polyoxyethylene-(150)-distearate;

(xiii) one or more optional epithelium conditioning agent selected from the group consisting of panthenol, and calcium panthotenate;

(xiv) one or more optional skin soothing agent selected from the group consisting of chamomile extract, azulenole, and bisabolol; and (xv) one or more optional disinfectant selected from the group consisting of menthol, camphor, lactic acid, citric acid, and ethyl alcohol.

* * * * *